United States Patent [19]

Sandler et al.

[11] Patent Number: 5,614,650
[45] Date of Patent: Mar. 25, 1997

[54] ZIRCONIUM COMPOUNDS OF SULFONIC ACIDS

[76] Inventors: Stanley R. Sandler, 221 Hemlock La., Delaware, Pa. 19064; Michael D. Gernon, 117 Scarlet Oak Dr., Montgomery, Pa. 19406; Jacques Ragot, 10 Residence Tournemire 91940 Les Ulis, Paris, France

[21] Appl. No.: 399,670

[22] Filed: Mar. 7, 1995

[51] Int. Cl.$^6$ .................................. C07H 7/00
[52] U.S. Cl. ........................................... 556/54
[58] Field of Search ................................. 556/54

[56] References Cited

U.S. PATENT DOCUMENTS

| 4,202,990 | 5/1980 | Murakami et al. | 560/217 |
| 4,609,745 | 9/1986 | Barfurth et al. | 556/40 |
| 5,084,586 | 1/1992 | Faroog | 556/181 |

OTHER PUBLICATIONS

"Reactions of Flourinated Acid Anhydrides with Metal Alkoxides", Niyogi et al., J. of Fluor. Chem. 66 (1994), pp. 153–158.

"Zur Chemie der Perfluroalkansulfonsäuren", Schmeisser et al., Chem. Ber. 103 (1970), pp. 868–879.

Primary Examiner—Porfirio Nazario-Gonzalez

[57] ABSTRACT

Novel zirconium compounds of sulfonic acids are disclosed which have the following general formula:

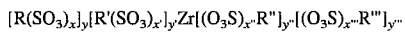

where R, R', R", R'" are independently substituted or unsubstituted, alkyl, alkylene, aryl or alkaryl radicals and x, x', x", x"', y, y', y" and y"' are sufficient in value to supply 4 sulfonate groups to the molecule, and the use of such zirconium compounds as catalysts in organic chemical reactions.

23 Claims, 2 Drawing Sheets

ZIRCONIUM COMPOUNDS OF SULFONIC ACIDS

BACKGROUND OF THE INVENTION

This invention relates to certain novel zirconium compounds of sulfonic acids. More particularly, it relates to zirconium compounds of substituted (functionalized) and unsubstituted mono- , di- , and polysulfonic acids.

The novel compounds of this invention are useful as recyclable catalysts for various organic chemical reactions, as, for example, in the production of esters and polyesters.

There is a general need in industry for recyclable catalysts with good catalytic activity. Good catalytic activity is often obtained with soluble catalysts (i.e., compounds soluble in the reaction medium), but such catalysts can be difficult to remove from the final product. Soluble catalysts always present a potential product contamination problem, and soluble catalysts must often times be washed out of products which can't be distilled (away from the catalyst). Recyclable catalysts are environmentally friendly, as recycling reduces the (total) amount of material requiring disposal. The catalysts of this invention can be used as mostly insoluble solid (recyclable) catalysts for the production, for example, of esters by either direct esterification or transesterification. Other solid (recyclable) catalysts have been used in esterification, but such catalysts (e.g. ion-exchange resin catalysts—Amberlyst® 15) generally have use temperature limitations (approx. 100°–110° C.). The zirconium compounds of this invention, when compared to ion exchange resins, generally have an extended range of permissible operating temperatures.

Zirconium methanesulfonate has an advantage over other common transesterification catalysts, such as tetrabutyl titanate and zirconium acetyl acetonate, in that it is not deactivated by the water sometimes present in the ester/alcohol reactants. Many common transesterification catalysts require anhydrous reaction conditions (i.e., predried reactants), and the manufacture of esters using such catalysts requires an additional drying step in the preparation process. For the preparation of propyl propionate via transesterification of methyl propionate with 1-propanol, the water sensitivity of common transesterification catalysts is clearly shown by plotting the % propyl propionate formed versus time for reactions employing dried and undried reactants with a variety of common catalysts—(See FIG. 1 of the drawings).

THE PRIOR ART

The various mono- , di- and polysulfonic acids used to form the zirconium compounds of this invention are generally known in the art. For example, the preparation of the starting monosulfonic acids is disclosed, e.g., in U.S. Pat. Nos. 3,948,922 and 4,859,373, and U.K. Patent No. 1,350, 328. Disulfonic acids are disclosed, for example, in the Journal of Organic Chemistry 30 pp.515–517 (1965) by Grot, W. G. in the article entitled "Sulfonation of Acetone with Fuming Sulfuric Acid". Polysulfonic acids are disclosed, for example, in Beilsteins Handbuch, "Der Organischen Chemie", 4th Ed., Zweiter Band, Erster Teil, (1960) EIII2, p. 51; and Vierter Band, Erster Teil (1962) EIII4, pp. 41–42. Further, poly(vinylsulfonic acid) [CAS#25053-27-4] is available from Aldrich Chemical Co. (Catalog #18, pp. 282-6), and poly (vinylphenylsulfonic acid) cross-linked by divinyl benzene (Amberlyst® 15 ion exchange resin) [CAS #9037-24-5] is available from Rohm & Haas Co.

Various metal salts of sulfonic acids are known including zirconium trifluoromethanesulfonate, Niyogi et al., Journal Fluorine Chemistry, 66 (1994), pp. 153–158, and Schmeisser et al., Chem. Ber., 103 (1970) 868–879. Niyogi et al. disclose some reactions of fluorinated acid anhydrides with metal oxides. In particular, the zirconium salt of trifluoromethanesulfonate is prepared by reacting zirconium ethoxide with trifluoromethanesulfonic anhydride. Schmeisser et al. disclose the preparation of the perfluoroalkanesulfonate of zirconium by reacting zirconium chloride with trifluoromethanesulfonic acid.

These methods of preparing perfluoroalkanesulfonic acid zirconium salts rely on the driving force provided by the stronger acidity of the acid employed relative to the conjugate acid of the counterion present in the zirconium compound starting material. The perfluorosulfonic acids have very high acidity making it easily possible to form salts of tetravalent zirconium. It is well known that the very high acidity of perfluoroalkanesulfonic acids (e.g. triflic acid) can be used to advantage in a number of chemical reactions, but the use of the corresponding non-fluoronated alkanesulfonic acid (e.g. methanesulfonic acid) in similar reactions is oftentimes unsuccessful. The extension of a reaction utilizing a perfluroalkanesulfonic acid to the corresponding, but considerable weaker in acidity, non-fluoronated alkanesulfonic acid, is not obvious, and the compounds derived from such an extension are novel and unexpected.

STATEMENT OF THE INVENTION

This invention comprises zirconium compounds of sulfonic acids having the general formula

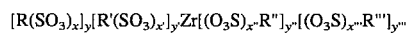

where R, R',R" and R'" are independently substituted or unsubstituted alkyl, alkylene, aryl or alkaryl radicals, x is an integer of from 1 to 4, x', x" and x'" are 1 to 3, y is 1 to 4, and y', y" and y'" are 0 to 3, provided that the values of x, x', x", x'", y, y', y" and y'" are sufficient to supply 4 sulfonate groups to the molecule.

THE DRAWING

DETAILED DESCRIPTION OF THE INVENTION

Figure 1:
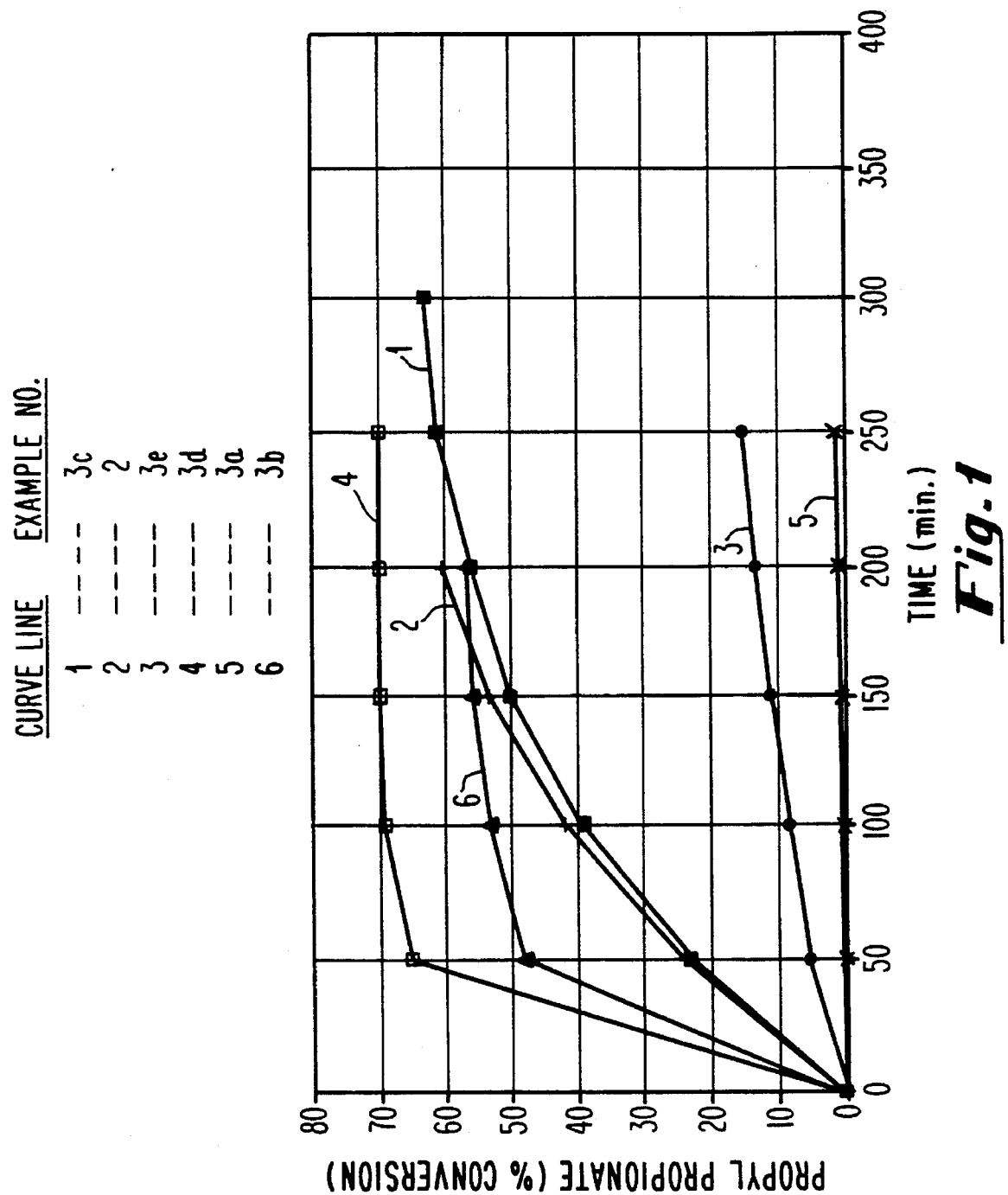
FIG. 1 is a graph representation of the conversion in percent of propyl propionate vs. time in several transesterification reactions of methyl propionate with 1-propanol using various catalysts, as carried out in Examples 2, 3a, 3b, 3c, 3d and 3e.

The novel compounds of this invention are zirconium compounds of sulfonic acids having the general structure

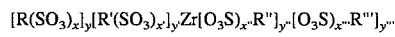

wherein R, R' R" and R'" are independently substituted or unsubstituted alkyl, alkylene, aryl or alkaryl radicals, x is an integer of from 1 to 4, x', x" and x'" are 1 to 3, y is 1 to 4, and y', y" and Y'" are 0 to 3, provided that the values of x, x', x", x''', y, y', y" and y''' are sufficient, in combination, to supply 4 sulfonate groups to the molecule. The disclosed zirconium compounds are usually ionizable salts but may also be nonionizable complexes. The substituents of R, R', R" and R''' may be, independently, any functional group, for example, hydroxy, keto, nitro, cyano and the like. Where R, R', R" and/or R''' are alkyl or alkylene, the radical may be straight or branch chained and preferably contains from 1 to 8, more preferably 1 to 4 carbon atoms. Where R, R', R" and/or R''' are aryl or alkylaryl, they will contain from 6 to 14, more preferably from 6 to 10 carbon atoms. These zirconium compounds may be deposited on clays, aluminas or other inert supports and used effectively as catalysts. The novel sulfonic acid zirconium compounds, supported or unsupported, can be successfully used as catalysts in a wide variety of organic reactions such as transesterification, direct esterification, alkylation, etherification, condensation, polymer-forming reactions, and others.

Examples of the compounds of this invention, in accordance with their proposed general structures, are:

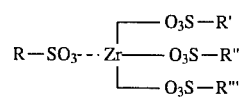

I a) 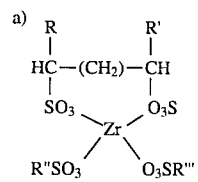 b) 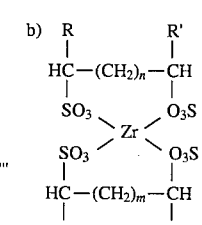

n and m are at least 1 c) 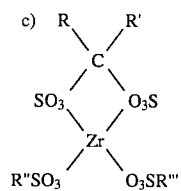

d) 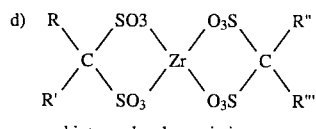

and intermolecular variations.

a) 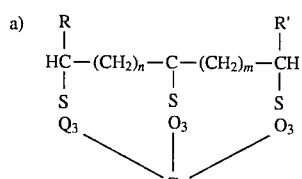

n and m are at least 1 b) 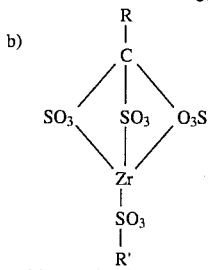

and intermolecular variations.

a) 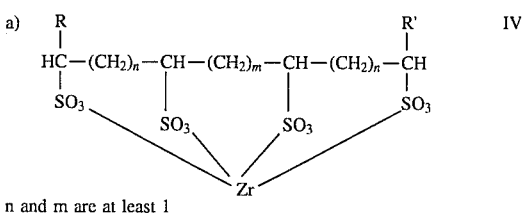 IV n and m are at least 1 b) 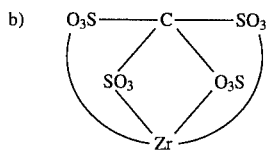

and intermolecular variations c) 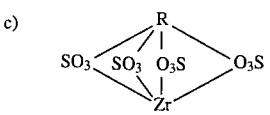

d) 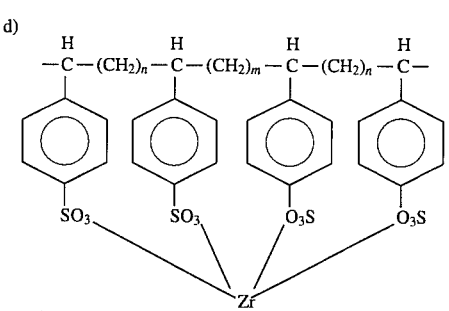

n and m are at least 1

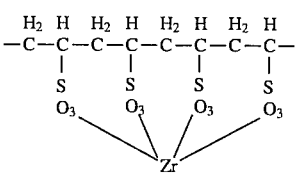

A number of preparative techniques can be used to synthesize the zirconium compounds of sulfonic acids. For example, the zirconium alkoxide may be reacted with the desired sulfonic acid in an inert atmosphere with cooling to precipitate the desired salt. Another procedure reacts zirconium tetrachloride with the desired sulfonic acid in a solvent medium (e.g. $CCl_4$) under an inert atmosphere. A continuous flow of inert gas and/or the use of vacuum, produces, after the displacement of HCl, the zirconium compound of the selected sulfonic acid.

The following examples are included to demonstrate the manufacture of novel zirconium sulfonate compounds, and the use of such zirconium compounds as catalysts.

Example 1

Preparation of Zirconium Methanesulfonate

A 1 liter, 3-necked round bottom flask which had been dried was equipped with a condenser, caustic trap, thermometer, and an addition funnel. Under a nitrogen atmosphere, the flask was charged with 250 ml of dry carbon tetrachloride ($CCl_4$), stirring was initiated, and this was followed by 40.0 g (0.42 mole) of anhydrous methanesulfonic acid (MSA) and 4.0 g (0.023 mole) of MSA anhydride (added as a drying agent). Typically, the water content of the reaction solution was found by Karl Fischer analysis to be 16 ppm. Following a satisfactory analysis for water content (i.e., below 25 ppm), 23.3 g (0.1 mole) of zirconium tetrachloride was added dropwise to the solution over 1 hour during which time a white precipitate formed and gaseous HCl evolution was observed. The evolved HCl(g) was swept out of the reaction flask and through a caustic trap with a slow stream of nitrogen. A 50 ml portion of $CCl_4$ was added to lower the viscosity of the mixture, and with $N_2(g)$ flowing, the reaction was stirred for 16 hours at room temperature. Following this, the reaction mixture was heated to 40° C. until no more HCl evolution was observed (normally about three hours). The reaction was cooled to room temperature. The solid product, which precipitated from the reaction solution, was collected by vacuum filtration under nitrogen. The product was washed twice with dry $CCl_4$. The product was split into two portions (portion one was approximately twice the size of portion two). The first portion was washed twice with ether and acetonitrile before removal of the volatiles in-vacuo. After obtaining a constant weight under vacuum, the first portion weighed 21.9 g, while the second portion weighed 11.1 g as is, for a total of 33.0 g, (70% yield). Both lots were analyzed.

| | |
|---|---|
| Calc'd (M.W. 471.2) $Zr(O_3S\ CH_3)_4$: | Zr, 27.2%; S, 19.3% |
| Found: Lot #1 | Zr, 27.3%; S, 19.1% |
| Found: Lot #2 | Zr, 27.4%; S, 19.4% |

The NMR and infrared spectrum support the structure for this new composition as $Zr(O_3S\ CH_3)_4$.

The following table illustrates the operable and preferred limits for the preparation of typical zirconium tetraalkanesulfonates;

Example 2

Transesterification of Methyl Propionate with 1-Propanol

To a 250 ml round bottom flask equipped with a magnetic stirring bar, reflux condenser and thermocouple probe was added 44.52 g of methyl propionate (0.51 mole), which had been previously dried for 12 hours over #4A molecular sieves, and 0.40 g (0.085 mole) zirconium tetramethanesulfonate. The mixture was heated to reflux (about 80° C.) and 1-propanol (10.16 g or 0.17 mole) was added all at once (time t=0). Samples were taken regularly and analyzed by gas chromatography (GC).

In this, and in all of the following examples, the catalyst was used in amount of 0.5 mole % of the 1-propanol (limiting reactant) and the mole ratio of mnethyl propionate to 1-propanol was 3.0/1.0.

Using empirically derived calibration curves that correlated GC peak area % values with the weight % of ester product and % conversion (using prepared standards), the progress of the above transesterification reaction was followed by GC. Representative experimental data is shown on Table 2 below and in FIGS. 1 and 2 of the Drawing (curve Lines 2)

TABLE 1

| Parameter | Operable Limits | | Preferred Limits | |
|---|---|---|---|---|
| | Lower | Upper | Lower | Upper |
| $Zr(O_3SR)_4$ [e.g., $Zr(O_3SCH_3)_4$] | | | | |
| Temperature (°C.) | 0 | 130 | 10 | 80 |
| Pressure (atmospheres) | 0.1 | 10 | 0.5 | 1.5 |
| Reaction Time Hours | 1 | 200 | 2 | 10 |
| Reactants Mole-Ratio $ZrX_4/RSO_3H/(RSO_3)_2O$ [e.g., $ZrCl_4/CH_3SO_3H/(CH_3SO_2)_2O$] | 1/4/0.1 | 1/20/0.5 | 1/4.2/0.2 | 1/5/0.3 |
| Solvents | $CCl_4$, $CHCl_3$ $CH_2Cl_2$, AcCN, $Et_2O$, etc. | | $CCl_4$ $CHCl_3$ | |
| Concentration of Reactants $ZrX_4$ & $RSO_3H$ (Weight % total and M Zr) | .1 wt %, 0.01M | 100 wt %, 2.0M | 10 wt %, 0.2M | 20 wt %, 0.8M |
| Inert Gas Flow (Nitrogen, cc/min) | 0.01 | 5000 | 10 | 200 |

TABLE 2

| Time (min) | Temp (oil Bath) | °C. (Rxn Flask) | % CH₃OH | % Methyl propionate | % 1-propanol | % propyl propionate | % conversion |
| --- | --- | --- | --- | --- | --- | --- | --- |
| 0.1 | 120 | 78 | 0.10 | 75.97 | 24.50 | 0.15 | 0.34 |
| 2 | 120 | 79 | 0.18 | 74.78 | 24.22 | 0.73 | 1.67 |
| 9 | 120 | 79 | 0.50 | 73.54 | 23.13 | 2.75 | 6.28 |
| 23 | 120 | 78 | 0.95 | 71.58 | 21.47 | 5.91 | 13.49 |
| 47 | 120 | 76.5 | 1.70 | 68.28 | 18.91 | 11.01 | 25.12 |
| 97 | 120 | 75 | 2.76 | 64.20 | 14.73 | 18.19 | 44.51 |
| 157 | 120 | 74 | 3.37 | 61.49 | 12.16 | 22.87 | 52.19 |
| 197 | 120 | 73 | 3.71 | 60.21 | 10.98 | 24.99 | 53.03 |
| 300 | 120 | 73 | 4.21 | 56.41 | 9.24 | 29.95 | 68.35 |

Example 3 (Comparison)

Transesterification of Methyl Propionate with 1-Propanol using Dibutyltin Oxide as a Catalyst.

In a manner similar to Example 2, a flask was charged with 87.28 g (1.0 mole) of methyl propionate and 0.41 g of dibutyl tin oxide catalyst. The mixture was brought to reflux and 1-propanol (19.6 g, 0.33 moles) was added all at once. As in Example 2, samples were taken at regular intervals for GC analyses. Representative data is shown in the table below;

TABLE 3

| Time (min) | Temp (oil Bath) | °C. (Rxn Flask) | % CH₃OH | % Methyl propionate | % 1-propanol | % propyl propionate | % conversion |
| --- | --- | --- | --- | --- | --- | --- | --- |
| 0.1 | 105 | 79 | 0.02 | 75.27 | 24.32 | 0.04 | 0.09 |
| 25 | 105 | 78 | 0.23 | 74.29 | 23.76 | 1.34 | 3.10 |
| 45 | 105 | 78 | 0.47 | 73.63 | 22.86 | 2.65 | 6.13 |
| 65 | 95 | 77.5 | 0.68 | 72.52 | 22.09 | 4.29 | 9.93 |
| 105 | 95 | 77 | 1.18 | 70.45 | 20.35 | 7.66 | 17.72 |
| 175 | 95 | 76 | 1.76 | 68.10 | 18.03 | 11.51 | 26.77 |
| 225 | 95 | 75 | 2.18 | 66.77 | 16.89 | 13.59 | 31.44 |
| 280 | 95 | 75 | 2.37 | 65.62 | 15.99 | 15.43 | 35.70 |

As a transesterification catalyst, zirconium tetramethanesulfonate is superior to an equimolar amount of the commercial tin catalyst of Example 3. In addition, the commercial tin catalyst of Example 3 is completely soluble in the reaction mixture, while the zirconium tetramethanesulfonate catalyst of Example 2 is practically insoluble in the reaction medium. Insoluble, solid catalysts are convenient in that they can be filtered off for easy disposal and/or recycling and do not cause metal contamination of the products (especially in the case where the product can't be distilled).

The following comparative examples, are based on the procedure of the above Example 3 but utilize different catalysts, or zirconium tetramethanesulfonate without drying (standard procedure =SP–about 1000–1500 ppm H₂O content) or with drying (anhydrous procedure =AP–about 100–600 ppm H₂O content after drying with Molecular Sieves #4a). 0.5 mole % of catalyst is used in each example, based on the 1-propanol reactant. As in Example 3, the mole ratio of methyl propionate to 1-propanol in each comparative example was 3.0/1.0.

Example 3a

Transesterification of methyl propionate with 1-propanol, without drying of the reactants, was carried out in the presence of titanium tetrabutoxide obtained from E. I. duPont & Co. The conversion results are reported in FIG. 1 of the Drawing (curve line 5).

Example 3b

Transesterification of methyl propionate with 1-propanol with the reactants dried to 600 ppm water content, was carried out in the presence of titanium tetrabutoxide as in Example 3a. The conversion results are reported in FIG. 1 (curve line 6).

Example 3c

The transesterification reaction of Example 3a was carried out again except that the titanium catalyst was replaced with zirconium tetramethanesulfonate, without drying. The conversion results are reported in FIGS. 1 and 2 of the Drawing (curve lines 1).

Example 3d

The transesterification reaction of Example 3a was carried out again except that the titanium catalyst was replaced with zirconium acetonyl acetonate with drying to reduce its water content to less than 600 ppm. The conversion result is shown in FIG. 1 (curve line 4).

Example 3e

The transesterification reaction of Example 3d was again carried out except that the zirconium acetonyl acetonate catalyst was used without drying. The conversion result is shown in FIG. 1 (curve line 3).

Examples 3f and g

Figure 2:
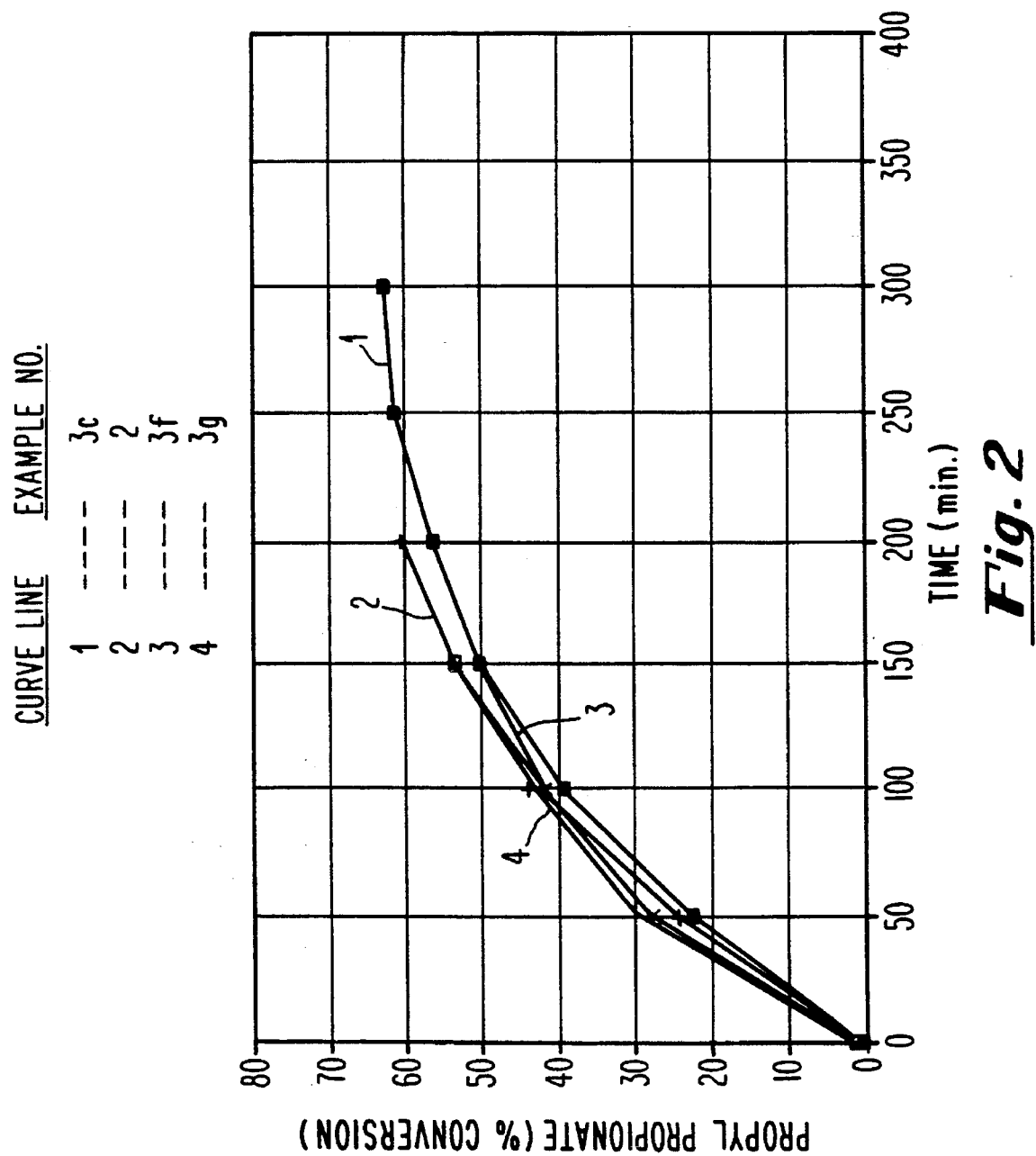
FIG. 2 is a graph representation of the conversion in percent of propyl propionate vs. time in several transesterification reactions of methyl propionate with 1-propanol using zirconium methanesulfonate catalysts which have different water contents in accordance with Examples 2, 3c, 3f and 3g.

The transesterification reaction of Example 3c was repeated twice using the zirconium tetramethanesulfonate catalyst with added water; Example 3f contained 1000 ppm added water and Example 3g contained 3000 ppm added water in the catalyst. The conversion results are shown in FIG. 2 of the Drawing (curve lines 3 and 4).

FIG. 1 clearly demonstrates that zirconium methanesulfonate is not affected by the water content normally present in commercially available methyl propionate and 1-propanol (approx. 1000–1500 ppm), while titanium tetrabutoxide and zirconium acetonyl acetonate are ineffective in the presence of this amount of water. Additionally, FIG. 2 demonstrates that the presence of added water (1000–3000 ppm) to the zirconium methanesulfonate catalyst does not reduce its effectiveness as a catalyst in the transesterification reaction.

Example 4 (Condensation Reaction)

To a mixture of 30% Cymel 303 (hexamethoxymethylmelamine 98% from Cytec Inc.) and 70% Joncryl 500 (hydroxyacrylic resin polymer, OH#140, 80% solids in methyl amyl ketone from S. C. Johnson Inc) was added 0.18 mmol catalyst (see table below). The formulation was cured at 115C and the time to reach a viscosity of 2500 cps was noted as the gel time. The catalyst concentration was 0.18 mmol based on the total weight for each of the experiments shown in the Table below. As shown, the zirconium methanesulfonate was compared to MSA and stannous methanesulfonate. Zirconium methanesulfonate (100%) had the same activity as free methanesulfonic acid.

TABLE 4

| CATALYST | SOLUBILITY | GEL TIME |
| --- | --- | --- |
| Methane sulfonic acid (MSA) | sol | 4.1 mins. |
| Stannous methane sulfonate | insol | 21.5 mins. |
| Stannous methane sulfonate/water (50%) | sol | 6.5 mins. |
| Stannous methane sulfonate | insol | 21.4 mins. |
| Stannous methane sulfonate/water (50%) | sol | 6.3 min |
| Zirconium methanesulfonate | sol | 4.0 min |
| Zirconium methanesulfonate/ water (50%) | sol | 7.4 min |

We claim:

1. A zirconium compound of a sulfonic acid having the following general formula:

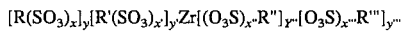

where R1, R', R" and R'" are independently substituted or unsubstituted alkyl, alkylene, aryl or alkaryl radicals, x is an integer of 1 to 4, x', x" and x'" are 1 to 3, y is 1 to 4, and y', y" and y'" are 0 to 3, provided that the values of x, x', x", x'", y, y', y", and y'" are sufficient to supply 4 sulfonate groups to the molecule.

2. The zirconium compound of claim 1 wherein x is 1, y is 4, y', y" and y'" are 0, and R is alkyl.

3. The zirconium compound of claim 2 wherein R has from 1 to 4 carbons.

4. The zirconium compound of claim 2 wherein R has 1 carbon.

5. The zirconium compound of claim 1 wherein x is 2, y is 2, y', y" and y'" are 0 and R is an alkylene radical.

6. The zirconium compound of claim 1 wherein x is 2, y is 2, y', y", y'" are 0, and R is an alkyl radical.

7. The zirconium compound of claim 1 wherein x is 2, y is 1, x' is 1, y' is 2, y" and y'" are 0 and R is alkylene and R' is alkyl.

8. The zirconium compound of claim 1 wherein x is 2, y is 1, x' is 1, y' is 2, y" and y'" are 0 and R and R' are alkyl radicals.

9. The zirconium compound of claim 1 wherein x is 2, y is 1, x' is 2, y' is 1, y" and y'" are 0 and R and R' are different alkylene radicals.

10. The zirconium compound of claim 5 wherein the alkylene radical has from 1 to 4 carbons.

11. The zirconium compound of claim 7 wherein the alkylene radicals have from 1 to 4 carbons.

12. The zirconium compound of claim 9 wherein the alkylene radicals have from 1 to 4 carbons.

13. The zirconium compound of claim 1 wherein x is 3, y is 1, x' is 1, y' is 1, y" and y'" are 0, and R and R' re alkyl.

14. The zirconium compound of claim 1 wherein x is 4, y is 1, y', y" and y'" are 0, and R is alkyl.

15. The zirconium compound of claim 13 wherein R and R' have 1 to 4 carbons.

16. The zirconium compound of claim 14 wherein R has 1 to 4 carbons.

17. The zirconium compound of claim 1 wherein R and R' are alkylene radicals which are segments of the same chain of a resinous addition polymer.

18. The zirconium compound of claim 17 wherein R" and R'" are alkylene radicals which are segments of the same chain of a resinous addition polymer.

19. The method of producing a chemical reaction which is a transesterification, direct esterification, alkylation, etherification, condensation or polymer-forming reaction comprising contacting at least two reactive chemicals, at least one of which is an organic chemical, and inducing a reaction between said reactive chemicals in the presence of a catalytic amount of a zirconium compound of a sulfonic acid of the general formula:

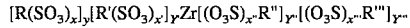

where R, R', R" and R'" are, independently, substituted or unsubstituted alkyl, alkylene, aryl or alkaryl radicals, x is an integer of 1 to 4, x', x" and x'" are 1 to 3, y is 1 to 4, and y', y" and y'" are 0 to 3, provided that the values of x, x', x", x'", y, y', y", and y'" are sufficient to supply 4 sulfonate groups to the molecule.

20. The method of claim 19 wherein the chemical reaction is an esterification reaction.

21. The method of claim 20 wherein zirconium compound of a sulfonic acid is zirconium alkanesulfonate having from 1 to 8 carbons.

22. The method of claim 21 wherein the zirconium alkanesulfonate is zirconium methanesulfonate.

23. The method of claim 19 wherein the chemical reaction is a condensation reaction.

* * * * *